United States Patent [19]

Martin et al.

[11] 4,160,327

[45] Jul. 10, 1979

[54] RACQUET GRIP FITTER SYSTEM

[76] Inventors: Rodger L. Martin, 340 Somerset Rd.;
Donald P. Nadwodny, 350 Somerset Rd., both of Pasadena, Md. 21122

[21] Appl. No.: 855,942

[22] Filed: Nov. 30, 1977

Related U.S. Application Data

[63] Continuation-in-part of Ser. No. 795,628, May 10, 1977, abandoned.

[51] Int. Cl.² ............................................... G01B 5/02
[52] U.S. Cl. .................................... 33/174 D; 33/2 R
[58] Field of Search ............................ 33/174 D, 2 R

[56] References Cited
U.S. PATENT DOCUMENTS 1,997,920  4/1935  Bliss ..................................... 33/2 R Primary Examiner—Willis Little
Attorney, Agent, or Firm—McClellan, Sr. John F.

[57] ABSTRACT

An instrument for indicating proper racquet-handle grip circumference for a given human-hand-characteristic size comprises a plate having a plate-longitudinal-alignment pointer and a scale spaced from the pointer for indicating characteristic length, and between the pointer and scale a plate orienting and laterally aligning fin for insertion between third and fourth human digits; transparent-scale and offset-scale embodiments are described and method is disclosed.

8 Claims, 5 Drawing Figures

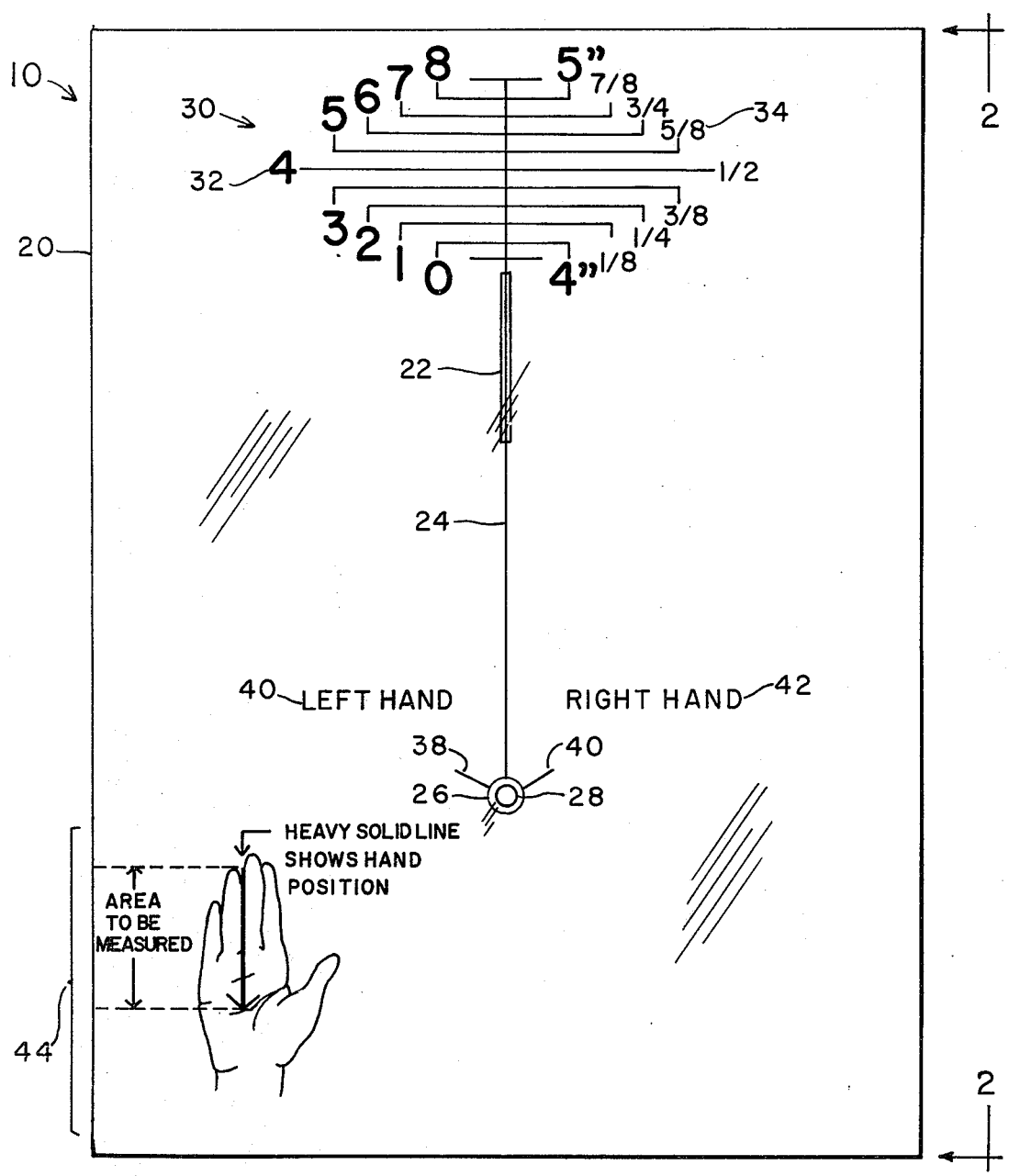
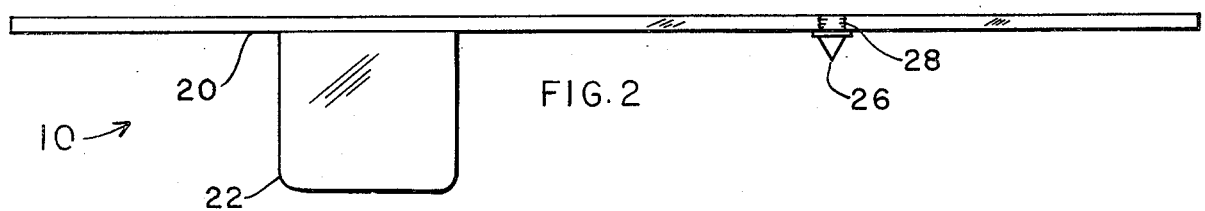
FIG. 1
FIG. 2

RACQUET GRIP FITTER SYSTEM

This application is a continuation in part of our co-pending application Ser. No. 795,628, filed may 10, 1977, and abandoned on filing of this application.

This invention relates generally to geometrical systems and particularly to a system for indicating proper racquet grip dimension in terms of human hand characteristics.

In the prior art glove-measurement systems have been disclosed measuring finger length, hand circumference and similar hand characteristics naturally of importance for glove fitting. However, such systems are at best distractive and less than marginally reliable as indicators of appropriate racquet handle dimension for a particular hand.

Proper fitting of racquet grip and hand is critical in serious tennis and has been generally a matter of "feel" not always reliable because of peculiarities of individual hands and the shifting relation of hand to racquet required in play.

As said by William Tilden in "Official Tennis Guide With the Official Rules 1942", copyright 1942 by A. S. Barnes and Company and generally accepted today:

"Forehand Ground Stroke Grip.—Hold the racket as if it were standing on the edge of the frame, the handle pointing toward you, the short strings perpendicular to the ground, the long strings parallel to it. Then 'shake hands' with it—literally. - - - ;

Backhand Ground Stroke Grip. - - - Move the hand one-quarter of a circle on the handle, backward, so that the hand rests directly on top of the handle, the knuckles of the hand pointing to the sky. - - - ;

Service Grip. - - - Take your forehand grip and then turn the hand halfway back to the backhand position. - - -."

A principal object of the present invention is to provide a system for assuring selection of the optimum racquet-grip measurement for a particular hand quickly and surely by taking into account certain key characteristics of the hand not heretofore generally appreciated, using apparatus not before known.

Further objects are to provide a system as described in which is simple, economical, easy to learn and to use and is reliable and accurate, with the apparatus portion additionally being compact and attractive.

In brief summary given for cursive descriptive purposes only and not as limitation the invention includes an aligning system measuring between two points on a hand in units of racquet handle size.

The above and other objects and advantages of the invention will become more readily apparent on examination of the following description, including the drawings in which like reference numerals refer to like parts:

FIG. 1 is a plan view of a first embodiment;

FIG. 2 is a side elevational view of the first embodiment taken at 2—2, FIG. 1;

Figure 3:
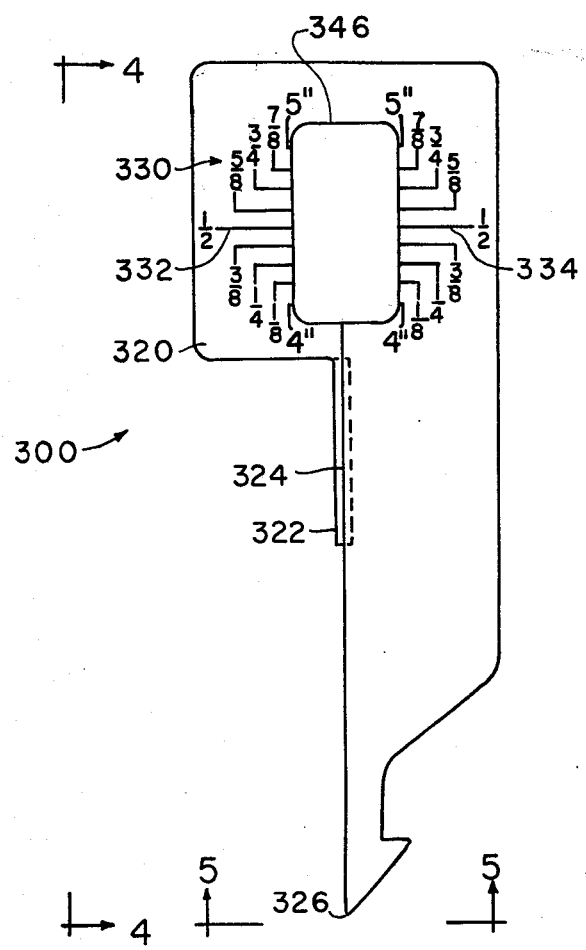
FIG. 3 is a plan view of a second embodiment.

FIGS. 1 and 2 show embodiment 10 of the invention in the form of a rectangular plate 20, which may be of any suitable rigid plastic, as for example a 6×8×⅛ inch (150×200×5 mm) sheet of transparent polystyrene.

Means for aligning the plate with a hand automatically in correct orientation to make a proper measurement comprises a fin 22 which is affixed to or integrally molded with the late, preferably along the centerline on the lower surface. Preferably a centerline 24 is marked on the plate. Adjacent one end of the centerline a pointer 26 provides means for pointing at a first location, on a hand, which may be affixed by screw threads 28 permitting adjustment of pointer length or substitution of pointers, permitting reaching into the arch of a particular palm without distortive flattening the hand, or may be intergrally molded. In either case, a conically pointed end is preferred, of about 45° included angle, giving good visibility around it combined with safety against needle-like hazards in ⅛ to ¼ in. length.

At the other end of the centerline a scale 30 of a plurality of lines traverse to the fin alignment and preferably crossing the centerline is supplied, on one side indicating in sets of units 32 international tennis-racquet handle - size designation and on the other side in equivalent units 34 of inches and fractional inches from the pointer (or other general units such as metric units if desired).

In operation according to a discovery which is part of this invention, measurement is made, preferably as follows, of the distance, along a line defined by juxtaposition of the second and third fingers, from the end of the ring finger to the second horizontal line crossing the palm.

a. First, the hand to be measured is extended horizontally, palm-side up and open but relaxed, with fingers together. Symmetry of the unit 10 equips it to measure either left hand or right hand, as desired.

b. Next the unit 10 is laid on the hand with pointer 26 at the palm and fin 22 protruding downwardly between the third and fourth (the middle and ring) fingers. Longitudinal extent of the relatively thin fin causes the unit 10 to orient with the hand properly and automatically.

c. The unit 10 is then adjusted by sliding it longitudinally, fin remaining between the adjoining fingers and maintaining orientation, until the pointer 26 points at and preferably for accuracy reaches into the arch of the palm to a particular location generally defining according to this invention the "center" of the palm, that is the intersection of the so-called "line of head" with the "line of fortune", or the central point of the "M" formed by lines in the palm. (The line of head is defined by the 11th Edition of Encyclopoedia Brittanica, Volume 20, page 650, as "the line starting above the head of the second metacarpal bone and crossing the hand to the middle of its ulnar border", and the line of fortune is described as "the vertical line descending from the middle of the wrist to end about the base of the middle finger".)

d. Finally, the scale is read at the end of the third or ring finger, giving the measurement from the "center" of the palm to it, along the line between the second and third fingers, in terms of fitting racquet grip diameter for the particular hand. Although not all hands are the same in proportion, this system of analogy works for at least nine out of every ten hands tried.

Further features evident in depiction of this embodiment are arrowhead lines 38 and 40 joining the centerline at angles of approximately 60° at the pointer, which have adjacent designations "left-hand" and "right-hand" 40, 42 respectively, and assist in aligning with lines or creases in the respective hands when positioning the pointer. At the lower left a representation of working parts of the unit in relation to a hand, diagram 44, shows how to use the unit. For maximum instructiveness, the diagram is reduced in scale and is parallel-offset from and lower than the scale, fin, centerline and pointer so that the upper portions of the plate may be grasped in use without obscuring the diagram.

Figure 4:
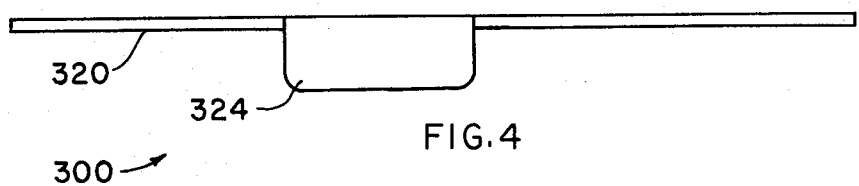
FIG. 4 is a side elevational view of the second embodiment, taken at 4—4, FIG. 3.
Figure 5:
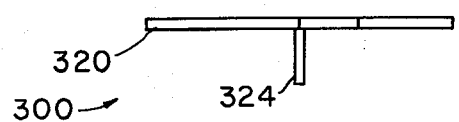
FIG. 5 is an end elevation view of the second embodiment taken at 5—5, FIG. 3.

FIGS. 3, 4 and 5 show a second embodiment 300 of the invention, which may be made of opaque material such as aluminum sheet, 1/16 inch (2.5 mm) thick, or other suitable material of appropriate thickness. For visibility, the pointer 326 may have a point oriented otherwise than directly toward the palm perpendicular to the plate as previously shown; it may incline or it may form the end of the plate as shown.

The fin 322 extends as before, longitudinally along the unit centerline 324, which may be substantially along an edge as shown making the centerline a definite physical feature, and downward to project between the second and third fingers.

The scale 330 preferably makes reading more reliable and provides room for the two sets of markings 332, 334 on the scale 330 extending across to both sides of an open window 346 which preferably is symmetrically defined by structure of the plate 320, making the unit easier to lay securely on either hand also. Graduations may be in selected units; inches are shown.

It is evident that the invention disclosed herein can be used in other ways than specifically described to achieve the same end. For example, even though not preferred and probably less accurate, the apparatus could be used in reverse orientation to that described.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by United States Letters Patent is:

1. A hand-measuring system for determining appropriate racquet handle circumference to fit particular human hands, comprising: means for aligning with the palm and fingers of a hand including a plate, a fixed fin as said plate at an intermediate location and projecting perpendicularly from one side thereof said fixed fin proportioned for longitudinally aligning with and extending between second and third fingers of a hand and maintaining longitudinal orientation of the plate; a fixed pointer on the plate in longitudinal alignment with said fin and proportioned for positioning by longitudinal sliding of the plate to point at the center of a palm of a hand, and fixed scale means on the plate for indicating distance along said alignment from the pointer, when the pointer is pointing at the center of a palm of a hand, to the end of the third finger of the hand.

2. A hand-measuring system as recited in claim 1, the pointer having protrusion from the plate proportioned for reaching into the arch of the palm of a hand.

3. A hand-measuring system as recited in claim 2, the pointer being conical in end shape and having detachable screw connection to the plate permitting adjustment and permitting substitution of a pointer of another size.

4. In a hand-measuring system as recited in claim 2, the fixed scale means a scale comprising a plurality of lines transverse to the direction of fin alignment, said plurality of lines extending to both sides of the fin alignment direction for adapting the hand-measuring system for measuring either a right or a left hand as desired.

5. A hand-measuring system as recited in claim 1, the pointer forming an end of the plate.

6. A hand-measuring system as recited in claim 1, the plate being transparent, the fin and pointer being visible through the plate for noting correct fin and pointer location on a said hand during said aligning and pointing, and the fixed scale means extending across the plate a distance making possible the measuring of either a right hand or a left hand as desired.

7. A hand-measuring system as recited in claim 1, the pointer forming an end of the plate unitary with the plate, the plate being opaque and having a window therein positioned relative to the fin and-pointer for viewing the end of the third finger of either a right hand or a left hand, and the fixed scale means extending in alignment on the respective sides of the window for measuring either a right hand or a left hand.

8. A hand-measuring system as recited in claim 7, a portion of the plate forming an edge in alignment with the fin for facilitating pointer positioning.

* * * * *